United States Patent [19]

Hausheer et al.

[11] Patent Number: 5,674,873
[45] Date of Patent: Oct. 7, 1997

[54] LACTONE STABLE FORMULATION OF 10-HYDROXY 7-ETHYL CAMPTOTHECIN AND METHODS FOR USES THEREOF

[75] Inventors: Frederick H. Hausheer; Kochat Haridas, both of San Antonio, Tex.

[73] Assignee: BioNumerik Pharmaceuticals, Inc., San Antonio, Tex.

[21] Appl. No.: 487,781

[22] Filed: Jun. 7, 1995

Related U.S. Application Data

[62] Division of Ser. No. 172,620, Dec. 22, 1993, Pat. No. 5,447,936.
[51] Int. Cl.$^6$ .................................................. A61K 31/44
[52] U.S. Cl. ........................................................ 514/283
[58] Field of Search ........................................... 514/283

[56] References Cited

U.S. PATENT DOCUMENTS

| | | | |
|---|---|---|---|
| 4,339,276 | 7/1982 | Miyasaka et al. | 491/22 |
| 4,399,276 | 8/1983 | Miyasaka et al. | 491/22 |
| 4,399,282 | 8/1983 | Miyasaka et al. | 491/147 |
| 4,473,692 | 9/1984 | Miyasaka et al. | 546/48 |
| 4,545,880 | 10/1985 | Miyasaka et al. | 204/158 |
| 4,684,630 | 8/1987 | Repta et al. | 514/49 |
| 4,734,284 | 3/1988 | Terada et al. | 546/48 |
| 4,778,891 | 10/1988 | Tagawa et al. | 546/18 |
| 5,061,800 | 10/1991 | Miyasaka et al. | 514/219 |
| 5,180,722 | 1/1993 | Wall et al. | 546/48 |
| 5,225,404 | 7/1993 | Giovannella et al. | |
| 5,227,380 | 7/1993 | Wall et al. | |

FOREIGN PATENT DOCUMENTS

| | | | |
|---|---|---|---|
| A 0 074 256 | 3/1983 | European Pat. Off. | |
| A 61 210 032 | 2/1987 | European Pat. Off. | |
| A 0 321 122 | 6/1989 | European Pat. Off. | |
| A 0 325 247 | 7/1989 | European Pat. Off. | |
| WOA 92 05785 | 4/1992 | European Pat. Off. | |
| A 0 540 099 | 5/1993 | European Pat. Off. | |
| 61-85319 | 4/1986 | Japan. | |
| 85319 | 4/1986 | Japan | 31/47 |
| 238098 | 10/1988 | Japan. | |
| 63-238098 | 10/1988 | Japan. | |
| 232888 | 10/1991 | Japan | 491/22 |
| 3-232888 | 10/1991 | Japan. | |
| 4-139187 | 5/1992 | Japan. | |
| 139187 | 5/1992 | Japan | 491/22 |

OTHER PUBLICATIONS

Akimoto, K., et al., Selective and Sensitive Determination of Lactone and Hydroxy Acid Forms of Camptothecin and Two Derivatives (CPT–11 and SN–38) by High Performance Liquid Chromatography with Fluorescence Detection. Journal of Chromatography, 588:165–170, 1991.

Taxotere, Topotecan, and CPT–11: Clinical Trials Confirm Early Promise. Oncology Times, written by O. Baer, pp. 8–10, May 1993.

Bates, T.R., et al., Solubilizing Properties of Bile Salt Solutions I—Effect of Temperature and Bile Salt Concentration On Solubilization of Gluthethimide, Griseofulvin and Hexestrol. Journal of Pharmaceutical Sciences, 55:191–199, 1966.

Bates, T.R., et al., Rates of Dissolution of Grisofulvin and Hexestrol in Bile Salt Solutions. Chem. Abstracts 65:8680b, 1966.

Bates, T.R., et al., Solubilizing Properties of Bile Salt Solutions on Glutethimide, Griseofulvin, and Hexestrol. Chem. Abstracts 65:15165a, 1966.

Clavel, M., et al., Phase I Study of the Camptothecin Analogue CPT–11, Administered Daily for 3 Consecutive Days. Proc. Amer. Assoc. Cancer Res. 3:83, 1992.

Creavan, P.J., et al., Plasma Camptothecin (NSC 100880) Levels During a 3–Day Course of Treatment: Relation to Dose and Toxicity. Cancer Chemotherapy Rep. 56:573–578, 1972.

Culine, S., et al., Phase I Study of the Camptothecin Analogue CPT–11, Using a Weekly Schedule. Proc. of Amer. Soc. Clin. Onc. 11:110, 1992.

Eckardt, J., et al., Topoisomerase I Inhibitors: Promising Novel Compounds. Contemporary Oncology, pp. 47–60, 1993.

Fukuoka, M., et al., A Phase II Study of CPT–11, A New Derivative of Camptothecin, for Previously Untreated Non Small–Cell Lung Cancer. J. Clin. Onc. 10(1):16–20, Jan. 1992.

Gionvanella, B.C., et al., DNA Topoisomerase I—Targeted Chemotherapy of Human Colon Cancer in Xenografts. Science 246:1046–1048, Nov. 1989.

Gottlieb, J.A., et al., Preliminary Pharmacologic and Clinical Evaluation of Camptothecin Sodium (NSC–100880). Cancer Chemotherapy Reports 54(6):461–470, Dec., 1970.

Gottlieb, J.A., et al, Treatment of Malignant Melanoma with Camptothecin, (NSC100880). Cancer Chemotherapy Reports 56(1):103–105, Feb., 1972.

Hsiang, Y.H., et al., Arrest of Replication Forks by Drug-–stabilized Topoisomerase I–DNA Cleavable Complexes as a Mechanism of Cell Killing by Camptothecin Analogues. Cancer Res. 49:5077–5082, Sep., 1989.

(List continued on next page.)

Primary Examiner—Jerome D. Goldberg
Attorney, Agent, or Firm—Thomas J. Dodd

[57] ABSTRACT

10-hydroxy 7-ethyl camptothecin (HECPT), an active metabolite of the camptothecin analog CPT-11, is poorly soluble in water. Because of its poor water solubility, HECPT has not been directly administered by parenteral or oral routes in human patients for the purpose of inhibiting the growth of cancer cells. There is also unpredictable interpatient variability in the metabolic production of HECPT from CPT-11 which limits the utility of CPT-11. This invention overcomes these limitations by teaching novel pharmaceutically acceptable lactone stable HECPT formulations for the direct administration of HECPT. The claimed invention also describes novel dosages, schedules, and routes of administration of the lactone stable HECPT formulations to patients with various forms of cancer.

30 Claims, No Drawings

OTHER PUBLICATIONS

Jaxel, C., et al., Structure Activity of Study of the Actions of Camptothecin Derivatives on Mammalian Topoisomerase I: Evidence for a Specific Receptor Site and A Relation to Antitumor Activity. Cancer Res. 49:1465–1469, Mar., 1989.

Kaneda, N., et al, Metabolism and Pharmacokinetics of the Camptothecin Analogue CPT–11 in the Mouse. Cancer Research 50:1715–1720, Mar., 1990.

Kano, Y., et al., Effects of CPT–11 in Combination With Other Anti-Cancer Agents in Culture. Int. J. Cancer 50:604–610, 1992.

Kanzawa, F., et al., Role of Carboxylesterase on Metabolism of Camptothecin Analog (CPT–11) in Non–Small Cell Lung Cancer Cell Line PC–7 Cells (Meeting Abstract). Proc. Annual Meet. Am. Assoc. Cancer Res. 33: A2552, 1992.

Kawato, Y., et al, Intracellular Roles of SN–38, a Metabolite of the Camptothecin Derivative CPT–11, in the Antitumor Effect of CPT–11. Cancer Res. 51:4187–4191, Aug., 1991.

Kingsbury, W.D., et al., Synthesis of Water–Soluble (Aminoalkyl) Camptothecin Analogues: Inhibition of Topoisomerase I and Antitumor Activity. J. Med. Chem. 34:98–107, 1991.

Kunimoto, T., et al., Antitumor Activity of 7–Ethyl–10–[4–(1–Piperidino)–1 Piperidino] Cabronyloxy–Camptothecin Against Murine Tumors. Cancer Res. 47:5944–5947, Nov., 1987.

Malone, M.H., et al., Desoxycholic Acid Enhancement of Orally Administered Reserpine. Journal of Pharmaceutical Sciences, 55(9):972–974, Sep., 1966.

Masuda, N., et al., CPT–11: A New Derivative of Camptothecin for the Treatment of Refractory or Relapsed Small–Cell Lung Cancer. J. Clin. Onc. 10(8):1225–1229, Aug., 1992.

Moertel, C.G., et al., Phase II Study of Camptothecin (NSC–100880) in the Treatment of Advanced Gastrointestinal Cancer. Cancer Chemotherapy Rep. 56(1):95–101, Feb., 1972.

Muggia, F.M., et al., Phase I Clinical Trial of Weekly and Daily Treatment With Camptothecin (NSC–100880): Correlation With Preclinical Studies. Cancer Chemotherapy Rep. 56(4):515–521, Aug., 1972.

Negoro, S., et al., Phase I Study of Weekly Intravenous Infusions of CPT–11, a New Derivative of Camptothecin, in the Treatment of Advanced Non–Small Cell Lung Cancer. JNCI 83(16):1164–1168, Aug., 1991.

Negoro, S., et al., Phase II Study of CPT–11, a New Camptothecin Derivative, in Small Cell Lung Cancer. Proc. Annu. Meet. of Amer. Soc. Clin. Onc. 10:241, Aug., 1991.

Niimi, S., et al., Mechanism of Cross–Resistance to a Camptothecin Analogue (CPT–11) in a Human Ovarian Cancer Cell Line Selected by Cisplatin. Cancer Res. 52:328–333, Jan., 1992.

Ohe, Y., et al., Phase I Study and Pharmacokinetics of CPT–11 With 5–Day Continuous Infusion. JNCI 84(12): 972–974, Jun., 1992.

Ohne, R., et al., An Early Phase II Study of CPT–11: A New Derivative of Camptothecin, for the Treatment of Leukemia and Lymphoma. J. Clin. Onc. 8(11):1907–1912, Nov., 1990.

Pommier, Y., et al., Camptothecins: Mechanism of Action and Resistance (Meeting Abstract). Cancer Investigation, Presented at the "Chemotherapy Foundation Symposium X Innovative Cancer Chemotherapy for Tomorrow", pp. 3–6, 1992.

Rothenberg, M.L., et al., A Phase I and Pharmacokinetic Trial of CPT–11 in Patients With Refractory Solid Tumors. Proceedings of Amer. Soc. Clin. Onc. 11:113, 1992.

Rotherberg, M.L., et al., Phase I and Pharmacokinetic Trial of Weekly CPT–11. Journal of Clinical Oncology. 11(11):2194–2204, Nov., 1993.

Rowinsky, E., et al., Phase I and Pharmacologic Study of CPT–11, A Semisynthetic Topoisomerase I–Targeting Agent, on a Single–Dose Schedule (Meeting Abstract). Proc. Annu. Meet. of Amer. Soc. Clin. Onc. 11:115,1992.

Sawada, S., et al., Synthesis and Antitumor Activity of 20 (S)–Camptothecin Derivatives: Carbonate–Linked, Water––Soluble, Derivatives of 7–Ethyl–10–Hydroxycamptothecin. Chem. Pharm. Bull. 39(6):1446–1454, 1991.

Shimada, Y., et al., Phase II Study of CPT–11, New Camptothecin Derivative, in the Patients with Metastatic Colorectal Cancer. Proc. of Amer. Soc. Clin. Onc. 10:135, Mar., 1991.

Takeuchi, S., et al., Late Phase II Study of CPT–11, A Topoisomerase I Inhibitor, in Advanced Cervical Carcinoma (CC) (Meeting Abstract). Proc. Annu. Meet. of Amer. Soc. Clin. Onc. 11:224, 1992.

Wall, M.E., et al., Plant Anti–Tumor Agents I—The Isolation and Structure of Camptothecin, a Novel Alkaloidal Leulemia and Tumor Inhibitor from Camptothecin Acuminata. J.Amer.Chem.Soc. 88(16):3888–3890, Aug., 1966.

Westergaard, H., et al., The Mechanism Whereby Bile Acid Mycelles Increase the Rate of Fatty Acid and Cholesterol Uptake Into the Intestinal Mucosal Cell. Journal of Clinical Investigation, 58:97–108 Jul. 1976 Various Computer Searches.

Kawato, Y., et al., Antitumor Activity of ACamptothecin Derivative, CPT–11, Against Human Tumor Xenografts in Nude Mice. Cancer Chemother Pharmacol, 28:192–198, 1991.

Ejima, A., et al., Antitumor Agents V.1 Synthesis and Antileukemic Activity of E–Ring–Modified (RS)–Camptothecin Analogues, Chem. Pharm. Bull., 40(3):683–688, Mar., 1992.

Pommier, Y., et al., Chapter 9: Mammalian DNA Topoisomerase I and Its Inhibitors. In: Cancer Chemotherapy Eds. Hickman and Tritton, Publisher: Blackwell Scientific Publications, pp. 214–250, 1993.

Extra, J.M., et al., Phase I Study of CPT–11, A Camptothecin Analogue, Administered as a Weekly Infusion. Proc. Amer. Assoc. Cancer Res., 3:83, 1992.

Rowinsky, E., et al., Phase I and Pharmacologic Studies of Topotecan, A Novel Topoisomerase I Inhibitor Without and With G–CSF. Proc. Amer. Assoc. Cancer Res., 3:83, 1992.

Kuhn, J., et al., Pharmacokinetics of Topotecan Following a 30 Min Infusion or 3 Day Continuous Infusion. Proc. Amer. Assoc. Cancer Res., 3:83, 1992.

Pantazis, P., et al., Cytotoxic Efficacy of 9–Nitrocamptothecin in the Treatment of Human Malignant Melanoma Cells in Vitro. Cancer Research, 54:771–776, Feb., 1994.

Rowinsky, E.K., et al., Phase I and Pharmacological Study of the Novel Topoisomerase I Inhibitor 7–Ethyl–10–[4–(1–piperidino)–1–piperidino]carbonyloxycamptothecin (CPT–11) Administered as a Ninety–Minute Infusion Every 3 Weeks. Cancer Research, 54:427–436, Jan., 1994.

Nicholas, A.W., et al., Plant Antitumor Agents. 29. Synthesis and Biological Activity of Ring D and Ring E Modified Analogues of Camptothecin. J. Med. Chem. 33:978–985, 1990.

DeVita, Vincent T., Jr.; *Principles of Chemotherapy;* Cancer: Principles & Practices of Oncology, Fourth Edition:276–292, 1993.

LACTONE STABLE FORMULATION OF 10-HYDROXY 7-ETHYL CAMPTOTHECIN AND METHODS FOR USES THEREOF

Cross-Reference to Related Applications

This application is a divisional application of Ser. No. 08/172,620, filed Dec. 22, 1993, now issued as U.S. Pat. No. 5,447,936, issued Sep. 5, 1995.

BACKGROUND OF THE INVENTION

1. Field of the Invention 10-hydroxy 7-ethyl camptothecin ("HECPT") is an active metabolite of the camptothecin analog CPT-11. HECPT is also poorly soluble in water. Because of its poor water solubility, HECPT has not been directly administered by parenteral or oral routes in human subjects for the purpose of inhibiting the growth of cancer cells. This invention overcomes these limitations and claims novel pharmaceutically acceptable formulations of lactone stable HECPT, methods of administration of lactone stable HECPT, and antitumor compositions comprising solutions of lactone stable HECPT. Additionally, this invention claims novel dosages, schedules of administration, and routes of administration of HECPT formulations to humans with various forms of cancer. 2. Description of the Related Art

A. Introduction

Metabolic conversion of CPT-11 (a water soluble derivative of camptothecin) to its active metabolite 10-hydroxy 7-ethyl camptothecin (HECPT) varies from patient to patient and limits the utility of CPT-11 in achieving the highest plasma concentrations of HECPT which can be tolerated by the patient. HECPT's poor solubility in water has previously made the direct administration of HECPT impractical for the treatment of cancer. The conversion of CPT-11 to HECPT involves a putative carboxyl esterase enzyme, which is believed to be mainly responsible for the metabolic production of HECPT from CPT-11. Human lung cancer cell lines have been observed to convert less CPT-11 to HECPT than normal cells. The cancer cells' decreased metabolic conversion represents a form of resistance to CPT-11 and limits the utility of CPT-11 in terms of reliably and safely achieving adequate plasma concentrations of HECPT to inhibit the growth of cancer cells in humans.

Until now, HECPT has been considered unsuitable for direct clinical use because it is poorly soluble in water. One useful purpose of this invention is to formulate HECPT in a pharmaceutically acceptable manner using an organic solvent or a mixture of organic co-solvents to stabilize HECPT in the lactone ring form. It is this lactone stable HECPT which permits direct administration of HECPT to cancer patients. An additional purpose of this invention to provide certain indications, schedules, dosages and routes of administration of lactone stable HECPT for the purpose of treating cancer in humans.

The selection of suitable organic solvents for pharmaceutical dosage forms is limited to those which have a high degree of physiological safety. This invention describes administration of lactone stable HECPT in a pharmaceutically acceptable multi-solvent formulation, overcomes inter-patient variability and drug resistance related to CPT-11 conversion to HECPT and is useful in instances where human cancer cells, because of their altered enzymatic activity, resist metabolic conversion of CPT-11 to HECPT.

B. DNA Topoisomerases

Several clinically important anticancer drugs kill tumor cells by affecting DNA topoisomerases. Topoisomerases are essential nuclear enzymes that function in DNA replication and tertiary structural modifications, such as overwinding, underwinding, and catenation, which normally arise during replication, transcription, and perhaps other DNA processes. Two major topoisomerases that are ubiquitous to all eukaryotic cells: (1) Topoisomerase I (topo I) which cleaves single stranded DNA; and (2) Topoisomerase II (topo II) which cleaves double stranded DNA. Topoisomerase I is involved in DNA replication; it relieves the torsional strain introduced ahead of the moving replication fork.

Topoisomerase I purified from human colon carcinoma cells or calf thymus has been shown to be inhibited by (a) camptothecin, (b) a water soluble analog called "CPT-11," and (c) 10-hydroxy 7-ethyl camptothecin (HECPT) which is the proposed active metabolite of CPT-11. CPT-11, camptothecin, and an additional Topo I inhibitor, topotecan, has been in used in clinical trials to treat certain types of human cancer. For the purpose of this invention, camptothecin derivatives include CPT-11, 10-hydroxy 7-ethyl camptothecin (HECPT) and topotecan. These camptothecin derivatives use the same mechanism to inhibit Topo I; they stabilize the covalent complex of enzyme and strand-cleaved DNA, which is an intermediate in the catalytic mechanism. These compounds have no binding affinity for either isolated DNA or topoisomerase I but do bind with measurable affinity to the enzyme-DNA complex. The stabilization of the topoisomerase I "cleavable complex" by camptothecin, CPT-11, or HECPT is readily reversible.

Although camptothecin, CPT-11, or HECPT have no effect on topoisomerase II, camptothecin, CPT-11 and HECPT stabilize the "cleavable complex" in a manner analogous to the way in which epipodophyllotoxin glycosides and various anthracyclines inhibit topoisomerase II.

Inhibition of topoisomerase I by camptothecin, CPT-11, or HECPT induces protein-associated-DNA single-strand breaks. Virtually all of the DNA strand breaks observed in vitro cells treated with CPT-11 or HECPT are protein linked. However, an increase in unexplained protein-free breaks can be detected in L1210 cells treated with camptothecin. The compounds appear to produce identical DNA cleavage patterns in end-labeled linear DNA. It has not been demonstrated that CPT-11, camptothecin, or HECPT cleaves DNA in the absence of the topoisomerase I enzyme.

C. Activity of HECPT, Camptothecin and CPT-11 is Cell Cycle Specific

The activity of camptothecin, CPT-11, and HECPT is cell cycle specific. The greatest quantitative biochemical effect observed in cells exposed to HECPT is DNA single-strand breaks that occur during the S-phase. Because the S-phase is a relatively short phase of the cell cycle, longer exposure to the drugs results in increased cell killing. Brief exposure of tumor cells to the drugs produces little or no cell killing, and quiescent cells are refractory. These results are likely due to two factors:

(1) The drugs inhibit topoisomerase I reversibly. Although they may produce potentially lethal modifications of the DNA structure during DNA replication, the breaks may be repaired after washout of the drug; and (2) Cells treated with topo I inhibitors, such as CPT-11 and HECPT, tend to stay in GO of the cell cycle until the drug is removed and the cleaved DNA is repaired. Inhibitors of these enzymes can affect many aspects of cell metabolism including replication, transcription, recombination, and chromosomal segregation.

D. Lactone Form Stabilizes HECPT

Utilizing HPLC and NMR techniques, researchers have demonstrated that camptothecin, CPT-11, and HECPT undergo an alkaline, pH-dependent hydrolysis of the E-ring lactone. The slow reaction kinetics allow one to assess whether both the lactone and non-lactone forms of the drug stabilizes the topoisomerase I-cleaved DNA complex. Studies indicate that only the closed lactone form of the drug helps stabilize the cleavable complex. This observation provides reasoning for the high degree of CPT-11 and HECPT activity observed in solid tumor models. Tumor cells, particularly hypoxic cells prevalent in solid neoplasms, have lower intracellular pH levels than normal cells. At pH levels below 7.0, the closed form of CPT-11 (and presumably of HECPT) predominates. Thus, the inventors predict that HECPT will be more effective at inhibiting topoisomerase I in an acidic environment than in cells having higher intracellular pH levels. It is the object of this invention to provide lactone stable HECPT as the basis of the claimed subject matter. Lactone stable HECPT is defined as HECPT which is dissolved in DMI or DMA in the presence of a pharmaceutically acceptable acid. The presence of the acid stabilizes the lactone form of HECPT. For the purpose of this invention lactone stable HECPT and HECPT are used interchangeably.

E. Camptothecin, CPT-11 and Topotecan

In 1966, Wall and Wani isolated camptothecin from the plant, *Camptotheca acuminata*. In the early 1970's, camptothecin reached Phase I trials and was found to have antitumor activity, but it caused unpredictable myelosuppression and hemorrhagic cystitis. Phase II studies with sodium camptothecin were limited because they induced unpredictable and severe myelosuppression, gastrointestinal toxicity, hemorrhagic cystitis, and alopecia. Clinical trials with sodium camptothecin were eventually discontinued because of unpredictable toxicities.

Two camptothecin derivatives, CPT-11 and Topotecan, have less sporadic toxicities but retain significant activity of the parent compound. CPT-11 and Topotecan are currently undergoing Phase I and Phase II development in the United States. 10, 11 methylene dioxycamptothecin is reportedly very active in preclinical studies, but it is also reported to be relatively insoluble in water which limits its use in the clinic (Pommier, et al. 1992).

Tables 1 and 2 present dan summarizing Phase I and Phase II clinical trials of CPT-11. Neutropenia and diarrhea are the major reported, dose-limiting toxicities of CPT-11.

TABLE 1

PHASE I STUDIES CPT-11

| Investigator | Schedule | # Pts | Dose | Toxicity | Tumor Type |
|---|---|---|---|---|---|
| Clavel et al | 90 min. QDx 3 Q21 days | 37 | 115 mg/m$^2$/d (33–115) | Neutropenia* diarrhea, nausea and vomiting, alopecia | Breast (1 PR) Mesothelioma (1 PR) |
| Culine et al | 90 min. Q21 days | 59 | 150 mg/m$^2$/wk (50–150) | Neutropenia* diarrhea* vomiting, alopecia fatigue stomatitis Neutropenia* | esophagus (1 PR) cervix (1 PR) renal (1 PR) overian (1 PR) |
| Negoro et al | 30 min infusion weekly | 17 | 100 mg/m$^2$ (50–150) | Diarrhea*, N/V, alopecia, liver dysfunction | NS CLC (2 PRs) |
| Ohe et al | 120 hr CI Q3 wks | 36 | 40 mg/m$^2$/d (5–40) | Diarrhea* nausea and vomiting, thrombocytopenia, anemia, liver dysfunction Diarrhea* | None |
| Rothenberg et al | 90 mg QW × 4 Q42 days | 32 | 180 mg/m$^2$/wk (50–180) | Neutropenia, nausea, vomiting, alopecia | Colon Ca (2 PRs) |
| Rowinsky et al | 90 min infusion Q21 day | 32 | 240 mg/m$^2$ (100–345) | Neutropenia* vomiting, diarrhea abd. pain, flushing | Colon Ca (1 PR) Cervix Ca (1 PR) |

*Dose Limiting Toxicity

TABLE 2

CPT-11 PHASE II TRAILS

| Investigator | Tumor Type | Schedule | # Pts. | Response Rate | Reported Toxicities |
|---|---|---|---|---|---|
| Fukuoka et al | Untreated Non Small Cell Lung Cancer | 100 mg/m² weekday | 73 | (23/72) PRs 31.9% | Neutropenia diarrhea, nausea, vomiting, anorexia, alopecia |
| Masudu et al | Refractory or Relapsed Small Cell Lung Ca | 100 mg/m² weekly | 16 | (7/15) PRs 47% | Neutropenia, diarrhea pneumonitis (12.5%) |
| Negoro et al | Small Cell Lung Cancer | 100 mg/m²/week | 41 | 2 CRs and 7 PRs 33.3% | Neutropenia (38.6%) N/V (61.5%) diarrhea (53.8%) alopecia (40.0%) |
| Ohono et al | Leukemia/ Lymphoma | 200 mg Q3 No resp. 40 mg/m²Q0 × 5 34% PR 20 mg/m² bid × 7 25% RR | 62 | ** | Neutropenia (91%) Thrombocytopenia Gastrointestinal (76%) |
| Shimada et al | Colon cancer | 100 mg/m²/week or 150 mg/m²/Q 2 wks | 17 | 6/17(PR) 46% | Neutropenia (53%) N/V (35%) diarrhea (24%) |
| Takeuchi et al | Cervical cancer | 100 mg/m² weekly 150 mg/m² weeks | 69 | 5CR 8PR RR of 23.6% | Neutropenia (89%) N/V (51%) Diarrhea (39.1%) Alopecia (38.1%) |

**see text

F. HECPT is the Active Metabolite of CPT-11

Preclinical data, obtained by Barilero et al. on animals and more recently on humans, suggest that HECPT is the active metabolite of CPT-I1 in vivo. Several different researchers administered CPT-11 and HECPT intravenously during Phase I trials and recorded the peak plasma concentrations (CpMax) at the end of the infusions. An analysis of the published mean peak plasma concentrations indicates that approximately 1.5% to 9% of the administered CPT-11 (on a per/mg basis) is convened into HECPT. The pharmacokinetic data from 30-minute intravenous infusions show a lower percentage of conversion (~1.5%) of CPT-11 to HECPT than that observed following more prolonged infusions (~9% at 40 mg/m²/d X5). The reported half life of HECPT observed in humans following the administration of CPT-11 ranges from 8.8 to 39.0 hours.

The biochemical and pharmacological relationship between CPT-11 and HECPT, as well as the role these compounds play in killing cancer cells in vivo is not completely understood. Investigators studying in vitro tumor cell lines have reported that HECPT has a 3600-fold greater inhibitory activity than CPT-11 against topoisomerase I in P388 cells and that HECPT is approximately 1000-fold more potent in generating single-strand DNA breaks in MOLT3 cells (Kawato, et al (1991)). However, Kaneda et al. report that HECPT has little anti-tumor activity compared to CPT-11 in vivo. They base their findings on studies conducted using an intermittent bolus schedule (days 1, 5, and 9) and an i.p. route of administration with an intraperitoneal P388 tumor model in mice.

Ohe et al. suggest that HECPT is a more toxic moiety of CPT-11 and could be responsible for much of the toxicity attributed to CPT-11. However, these same investigators noted a lack of correlation between HECPT pharmacokinetics and dose or CPT-11 pharmacokinetics and toxicity in human subjects. Furthermore, Ohe et al. noted a large range of interpatient variability in the AUC of CPT-11 and its metabolism to HECPT, which may result in unpredictable variability in the pharmacokinetic behavior, clinical anti-tumor effects, and toxicity in the individual patient. The data Ohe et al. obtained (using a 5-day, continuous intravenous infusion of CPT-11) also suggests that the conversion of CPT-11 to HECPT is a saturable process. If this is so, the clinical approach to maximizing dose intensity of the active metabolite would impose additional limitations on the effective use of CPT-11.

In preclinical studies of xenografts of human tumors in nude mice, Kawato et al. report that the sensitivity of human tumors to CPT-11 is independent of their ability to produce HECPT and that the effectiveness of CPT-11 is not related to the ability of the tumor to produce HECPT. Kawato et al. suggests that HECPT production is likely to be mediated in the plasma or interstitial compartment. Kaneda et al. observed that the plasma concentration of HECPT in mice was maintained longer after CPT-11 administration than after treatment with HECPT and suggested that clinicians should maintain plasma levels of HECPT to enhance the antitumor activity of CPT-11.

One of the advantages of present invention provides clinicians with the ability to directly adjust the plasma levels of HECPT to the point of therapeutic tolerance by controlling the dose and the schedule of administration. The inventors contend that this should lead to a superior ability to achieve better antitumor activity and reduce interpatient variability of the plasma levels of HECPT.

The different observations made in these studies suggest that direct administration of HECPT by parenteral and oral administration could provide significant clinical benefit for the treatment of cancer. However, in the past, HECPT has been considered insufficiently water soluble for clinical use. The current invention overcomes the solubility problem by providing lactone stable pharmaceutically acceptable multisolvent formulations of HECPT for parenteral use and also oral HECPT formulations.

SUMMARY OF THE INVENTION

This invention involves the formulation and methods of use of lactone stable HECPT to treat cancer in humans. For the purposes of this invention, lactone stable HECPT and HECPT are used interchangeably. In the case of intravenous administration of HECPT, several schedules and various dosages produce sufficient levels of lactone stable HECPT to yield beneficial antitumor effects in humans. The effective levels of HECPT are reasonably safe in terms of the incidence and severity of specific side effects that may occur with administration and are acceptable within standard medical practice for patients undergoing treatment for cancer.

Direct administration of HECPT is likely to offer several important clinical advantages over administration of CPT-11. For example:

(1) direct administration of HECPT allows the clinician to tailor the administration of the active cytoxic species (lactone stable HECPT) to suit the patient's tolerance;

(2) direct administration of HECPT overcomes interpatient variability which may be due to polymorphism of key enzyme(s) in the metabolism of CPT-11 to HECPT; and (3) clinicians can more consistently optimize the drug dosage and schedule to achieve the maximum tolerated dose of HECPT (the active species) which is likely to lead to the most beneficial clinical anti-cancer effect.

Regarding the clinical utility of HECPT for the treatment of human cancer, this invention provides the following:

(1) methods of administering lactone stable HECPT to patients with cancer;

(2) solutions of lactone stable HECPT;

(3) antitumor compositions comprising lactone stable HECPT;

(4) stable formulations of lactone stable HECPT suitable for parenteral administration;

(5) pharmacologic schedules for achieving the maximum tolerated dose with acceptable clinical toxicity observed in standard clinical practice of cancer treatment;

(6) a novel oral formulation of HECPT; and (7) use of HECPT for the treatment of localized complications of cancer by direct administration via instillation into various body cavities.

HECPT Dissolved in Dimethylisosorbide or Dimethylacetamide and Acid

An embodiment of the claimed invention is a 10-hydroxy 7-ethyl camptothecin (HECPT) solution comprising HECPT dissolved in dimethylisosorbide (DMI) in the presence of a pharmaceutically acceptable acid or dissolved in dimethylacetamide (DMA) in the presence of a pharmaceutically acceptable acid.

The 10-hydroxy 7-ethyl camptothecin (HECPT) solution is prepared by dissolving the desired components in dimethylisosorbide (DMI) or dimethylacetamide (DMA). Dimethylisosorbide has been used as solvent for muscle relaxants (U.S. Pat. No. 3,699,230), tetracyclines (U.S. Pat. No. 3,219,529), aspirin (U.S. Pat. No. 4,228,162), and steroids (U.S. Pat. No. 4,082,881). DMI and DMA have very good toxicity profiles and are miscible with ethanol, propylene glycol, isopropyl myristate, water, diethyl ether, corn oil, acetone, cottonseed oil, and the like.

An object of the present invention is to provide a solution of HECPT in DMI or DMA. A concentrated solution is particularly useful as a filling solution for gelatin capsules. The solution may also be formulated for parenteral use providing a useful and practical means to dissolve the drug.

The present invention is prepared by dissolving the desired components in DMI or DMA and the resulting solution is then filtered and the filtrate collected. The amount of HECPT contained in the solution of this invention is not specifically restricted but may be any amount convenient for pharmaceutical purposes, and may be selected according to the dosage to be prepared. A preferred capsule filling solution contains from about 0.1 mg to about 3.0 mg of HECPT activity per ml of solution.

As a preferred embodiment of the claimed invention, the 10-hydroxy 7-ethyl camptothecin solution is prepared by dissolving the desired components in dimethylisosorbide (DMI) or dimethylacetamide (DMA) in the presence of a pharmaceutically acceptable acid.

A pharmaceutically acceptable acid is preferably included in the solutions of the present invention. Any pharmaceutically acceptable acid may be used; for example mineral acids such as hydrochloric acid; and organic carboxylic acids, such as tartaric, citric, succinic, fumaric, or maleic acids. An organic carboxylic acid is preferred, and citric acid is most preferred. The amount of acid used may be from about 0.005 to about 0.5 parts by weight of acid per part by weight of HECPT and preferably from about 0.01 to 0.3 part by weight of acid per part by weight of HECPT. Citric acid is preferably used in a proportion of from about 0.05 to about 0.1, and about 0.1 part by weight in the presence of taurocholic acid or a pharmaceutically acceptable salt thereof.

In the formulations provided by the instant invention, HECPT is both soluble and maintained in its active lactone form. The non-enzymatic conversion of the pH labile E ring from the closed lactone (active) to the open carboxylate form (inactive) is reduced by formulating HECPT under acidic pH conditions (<5.0). Thus, a water soluble acid is included to assure that an acidic pH value is maintained upon dilution to form the micellar solution. Examples of preferred solid water-soluble organic carboxylic acids effective in this invention include citric, gluconic, maleic, tartaric, or ascorbic acids. Other acids may be employed, but citric acid is most preferred.

Yet another embodiment of the claimed invention is that the solution of HECPT contains from about 0.1 mg to about 3.0 mg activity of 10-hydroxy 7-ethyl camptothecin per ml of solution. This concentration would be effective for both oral and parenteral administration of the HECPT.

When oral dosages are to be administered in a capsule form, it is clearly superior to have a concentrated solution of HECPT suitable for encapsulation within a soft or hard gelatin capsule. Concentrated solutions allow the preparation of capsules of smaller size which allows easier ingestion by the patient, and may also reduce the number of capsules to be swallowed. These factors are important in view of the generally poor condition of cancer patients.

Taurocholic acid, a bile acid, may enhance in the intestinal absorption of the drug in certain patients. The present invention takes advantage of the discovery that taurocholic acid, or a pharmaceutically acceptable salt thereof, when included with HECPT in a solution dosage composition, results in improved absorption of the drug following ingestion of the composition. It is believed that this is due to the formation of a micellar solution of HECPT on dilution thereof with the gastric contents.

The phenomenon of micellar solubilization of poorly water-soluble drugs mediated by bile acids, including taurocholic acid, has been previously reported with respect to glutethimide, hexestrol, griseofulvin (Bates et al.), reserpine (Malone et al.) and fatty acids and cholesterol (Westergaard et al.). The use of taurocholic acid or a pharmaceutically acceptable salt thereof in the present invention involves a pharmaceutical solution of HECPT which has the unique property of providing a stable apparent solution of the drug upon dilution thereof with from 1 to 100 volumes of water. The solution is stable and free of precipitate for a period of at least two hours; sufficient time to permit administration and absorption by the patient.

It has been observed with similar solutions of etoposide, a different insoluble anticancer drug, that the bioavailability of the drug following oral administration is substantially equivalent to that achieved by intravenous administration of a solution of etoposide (U.S. Pat. No. 4,713,246). Analogous to that of etoposide, it is believed that ingestion of the present dosage form of HECPT and resulting dilution thereof by the stomach contents, results in the formation of a micellar solution of HECPT in the stomach which is readily absorbed by the gastrointestinal tract. Applicants do not wish to be bound, however, by any theoretical explanation of the mechanism by which the superior oral bioavailability of the present HECPT formulation is achieved.

Antitumor Compositions Comprising HECPT

A preferred embodiment of the claimed invention is an antitumor composition comprising a solution of 10-hydroxy 7-ethyl camptothecin dissolved in dimethylisosorbide or dimethylacetamide containing from about 0.1 mg to about 3.0 mg 10-hydroxy 7-ethyl camptothecin activity per ml and containing from about 0.01 to about 0.9 part by weight of a pharmaceutically acceptable organic carboxylic acid per part by weight of 10-hydroxy 7-ethyl camptothecin. Inventors prefer to use 0.01 to 0.2 part by weight of a pharmaceutically acceptable organic carboxylic acid per pan by weight of 10-hydroxy 7-ethyl camptothecin.

An additional embodiment of the claimed subject matter is wherein said part by weight of a pharmaceutically organic carboxylic acid is from about 0.05 to about 0.1 part by weight per part by weight of 10-hydroxy 7-ethyl camptothecin and the acid is citric acid.

Another embodiment of this invention is an antitumor composition comprising a solution of 10-hydroxy 7-ethyl camptothecin dissolved in dimethylisosorbide or dimethylacetamide in the presence of a pharmaceutically acceptable acid, wherein said solution further comprises taurocholic acid or a pharmaceutically acceptable salt thereof, polyethylene glycol, and water.

Yet another embodiment of this invention is wherein the solution of antitumor composition contains for each part by weight of 10-hydroxy 7-ethyl camptothecin, 1–10 parts by weight of dimethylisosorbide or dimethylacetamide, 0.005–0.5 parts by weight of a pharmaceutically acceptable acid, 1–10 parts by weight of taurocholic acid or a pharmaceutically acceptable salt thereof, 1–10 parts by weight of polyethylene glycol, and 0.1–2.0 parts by weight water. An additional embodiment is wherein said acid is an organic carboxylic acid and the inventors prefer citric acid.

Another embodiment of the claimed invention is the antitumor composition further comprises a lower alcohol. Many different alcohols would be effective in this invention, but the inventors prefer to use ethanol. Another embodiment of the claimed invention is the antitumor composition further comprises glycerin as a co-solvent.

Yet another embodiment of this invention is an antitumor composition comprising a solution of 10-hydroxy 7-ethyl camptothecin dissolved in dimethylisosorbide or dimethylacetamide in the presence of a pharmaceutically acceptable acid, wherein said solution further comprises taurocholic acid or a pharmaceutically acceptable salt thereof, polyethylene glycol, water, ethanol, glycerin, and a buffer, such as sodium acetate, to maintain an acidic pH.

An additional embodiment of this invention is wherein said solution contains for each part by weight of 10-hydroxy 7-ethyl camptothecin, 1–10 parts by weight of dimethylisosorbide or dimethylacetamide, 0.005–0.5 parts by weight of a pharmaceutically acceptable acid, 1–10 parts by weight of taurocholic acid or a pharmaceutically acceptable salt thereof, 1–10 parts by weight of polyethylene glycol, 0.1–2 parts by weight of glycerin, 0.1–2 parts by weight of ethanol, 0.005–0.5 parts of a buffer, and 0.1–2.0 parts by weight water.

Another embodiment of this invention is wherein said polyethylene glycol has a molecular weight of about 300 and the antitumor composition further comprises a non-ionic surfactant. There are many different surfactants but the inventors prefer a poloxamer. The preferred poloxamer is poloxamer 407.

Yet another embodiment of this invention is an antitumor composition comprising a solution of 10-hydroxy 7-ethyl camptothecin dissolved in dimethylisosorbide or dimethylacetamide in the presence of a pharmaceutically acceptable acid, wherein said solution further comprises a lower alcohol, polyethylene glycol, and surfactant.

As a more preferred embodiment for this antitumor composition, the pharmaceutically acceptable organic acid is citric acid, the polyethylene glycol has a molecular weight of about 300, the lower alcohol is ethanol and the surfactant is polysorbate-80.

Another embodiment of this invention is an antitumor composition comprising a solution of about 0.1 mg to about 2.0 mg of 10-hydroxy 7-ethyl camptothecin dissolved in 1 to 10 parts of dimethylisosorbide or dimethylacetamide in the presence of about 0.1 to 0.5 parts of a pharmaceutically acceptable organic carboxylic acid. This antitumor composition further comprises about 5 to 9 parts by weight of polyethylene glycol, about 0.1 to 2.0 parts of a pharmaceutically acceptable alcohol, and about 1 to 10 parts of a non-ionic surfactant.

More preferred for this antitumor composition is when the acid is citric acid, the polyethylene glycol has a molecular weight of about 300, the alcohol is ethanol and the surfactant is polysorbate-80.

Another embodiment of this invention is an antitumor composition comprising a solution about 0.1 mg to about 2.0 mg of 10-hydroxy 7-ethyl camptothecin dissolved in 1 to 10 parts of dimethylisosorbide or dimethylacetamide in the presence of 0.1 to 0.5 parts of a pharmaceutically acceptable organic carboxylic acid. This solution further comprises about 0.1 to 2.0 parts of a pharmaceutically acceptable alcohol, and about 1 to about 10 parts of a non-ionic surfactant.

More specifically for this antitumor composition, the acid is citric acid, the alcohol is ethanol, and the non-ionic surfactant is comprised of polyoxyethylated castor oil.

Another embodiment of this invention is an antitumor composition comprising a solution of 0.1 mg to about 2.0 mg of 10-hydroxy 7-ethyl camptothecin dissolved in 1 to 10 parts of dimethylisosorbide or dimethylacetamide, wherein this solution further comprises about 1 to 10 parts polyoxyethylated castor oil, about 0.1 to 2 parts by weight dehydrated ethyl alcohol USP, and about 0.1 to 0.9 parts citric acid.

In a more preferred embodiment, HECPT is solubilized in a manner suitable for clinical use by forming a sterile, nonaqueous solution of 1 part of HECPT per 1 to 2 ml in a vehicle comprising dehydrated ethyl alcohol 0.1–2.0 parts by weight, benzyl alcohol 0.1–2.0 parts by weight, citric acid 0.1–0.9 parts by weight, polyethylene glycol (molecular weight 200–300) 4 to 10 parts by weight, polysorbate-80 (Tween 80) 1 to 10 parts, and dimethylisosorbide 1 to 10 parts in acidified medium with a pH of 3 to 4.

This preferred embodiment of an HECPT solution in dimethylisosorbide is summarized in the table as follows:

| Ingredients | Parts by Weight |
| --- | --- |
| 10-hydroxy 7-ethyl Camptothecin | 1 |
| EtOH | 0.1–2.0 |
| Benzyl Alcohol | 0.1–2.0 |
| Citric Acid | 0.1–0.5 |
| PEG 300 | 5–9 |
| Dimethylisosorbide | 1–10 |
| Polysorbate 80 (Tween-80) | 1–10 |

Another more preferred parenteral formulation comprises HECPT formulated for dilution prior to parenteral administration made of 1 part HECPT in 2 ml of nonaqueous solvents including 1 to 10 parts Cremaphor EL (polyoxyethylated castor oil), 0.1 to 2 parts dehydrated ethyl alcohol USP, dimethylisosorbide 1 to 10 parts, and citric acid 0.1–0.9 parts to adjust the final pH to between 3 to 4.

This preferred embodiment of an HECPT solution in dimethylisosorbide is as follows:

| Ingredients | Parts by Weight |
| --- | --- |
| 10-hydroxy 7-ethyl-Camptothecin | 1 |
| Cremaphor EL | 1–10 |
| EtOH | 0.1–2.0 |
| Citric Acid | 0.01–0.5 |
| Dimethylisosorbide | 1–10 |

Dosages and Schedules for Parenteral Administration of HECPT Compositions

Another embodiment of this invention is a method of administration of lactone stable HECPT to a patient with cancer comprising infusing a fixed amount of HECPT over a period of time and repeated at predetermined intervals.

A more specific embodiment of the claimed invention is a method for administration of HECPT to a patient with cancer comprising infusing from about 2.0 mg/m$^2$ to about 33.0 mg/m$^2$ of lactone stable HECPT over a duration of approximately 120 minutes every 21 to 28 days.

An additional embodiment of the claimed invention is a method for administration of HECPT to a patient with cancer comprising infusing from about 1.0 mg/m$^2$ to about 16.0 mg/m$^2$ of lactone stable HECPT over a duration of approximately 120 minutes for three consecutive days every 21 to 28 days.

Another embodiment of the claimed invention is a method for administration of HECPT to a patient with cancer comprising infusing from about 1.0 mg/m$^2$ to about 20.0 mg/m$^2$ of lactone stable HECPT over a duration of approximately 120 minutes given once per week for three consecutive weeks with 2 weeks rest after each 3 week cycle.

Another embodiment of the claimed invention is a method for administration of HECPT to a previously untreated patient with cancer comprising infusing from about 2.0 mg/m$^2$ to about 24.0 mg/m$^2$ of lactone stable HECPT over a duration of approximately 120 minutes given once per week for three consecutive weeks with 2 weeks rest after each 3 week cycle.

Yet another embodiment of the claimed invention is a method for administration of HECPT to a patient with cancer comprising continuously infusing from about 0.1 mg/m$^2$/d to about 6.0 mg/m$^2$/d of lactone stable HECPT over a duration of approximately 24 to 120 hours every 21 to 28 days.

Another embodiment of this invention when lactone stable HECPT is infused into a patient with cancer, is the HECPT is dissolved in dimethylisosorbide (DMI) in the presence of a pharmaceutically acceptable acid or the HECPT is dissolved in dimethylacetamide (DMA) in the presence of a pharmaceutically acceptable acid.

Dosages and Schedules for Oral Administration of HECPT Compositions

Another embodiment of this invention is a method of oral administration of HECPT to a patient with cancer comprising an mount of HECPT given, as a single dose or divided into smaller doses, over a specified amount of time and repeated after a fixed amount of time.

More specifically, another embodiment of this invention is a method for oral administration of HECPT to a patient with cancer comprising administering from about 2.5 mg/m$^2$ to about 100 mg/m$^2$ of lactone stable HECPT in single or divided dosages within a 24 hour period every 21 to 28 days.

Yet another embodiment of this invention is a method for oral administration of HECPT to a patient with cancer comprising administering from about 1.0 mg/m$^2$ to about 50 mg/m$^2$ of lactone stable HECPT daily in single or divided doses for three consecutive days every 21 to 28 days.

Another embodiment of this invention is a method for oral administration of HECPT to a patient with cancer comprising administering from about 1.0 mg/m$^2$ to about 60.0 mg/m$^2$ of lactone stable HECPT in single or divided dosages within a 24 hour period given once per week for three consecutive weeks with 2 weeks rest after each 3 week cycle.

Another embodiment of this invention is a method for oral administration of HECPT to a previously untreated patient with cancer comprising administering from about 2.0 mg/m$^2$ to about 75 mg/m$^2$ of lactone stable HECPT in single or divided doses within a 24 hour period once per week for three consecutive weeks with 2 weeks rest after each 3 week cycle.

For the purpose of this invention, a previously untreated patient is defined as a patient with cancer who has not been previously treated with any chemotherapeutic drugs.

An additional embodiment of this invention is a method for oral administration of HECPT to a patient with cancer comprising administering from about 0.5 mg/m$^2$/d to about 18.0 mg/m$^2$/d of lactone stable HECPT in single or divided daily doses administered within each 24 hour period for two to five consecutive days and repeated every 21 to 28 days.

Yet another embodiment of this invention for oral administration to a patient with cancer is the HECPT dissolved in dimethylisosorbide (DMI) in the presence of a pharmaceutically acceptable acid or the HECPT is dissolved in dimethylacetamide (DMA) in the presence of a pharmaceutically acceptable acid.

A further embodiment of this invention is the claimed composition and method of administering the composition by encapsulating the claimed formulations within a hard gelatin capsule. Yet another embodiment of the claimed composition and method of administering the composition is encapsulating the claimed formulations within a soft gelatin capsule. One of ordinary skill in the art will know that any of the claimed formulations adapted for oral administration can be used as the fill for the soft or hard gelatin capsule.

A more specific embodiment of the claimed invention is an oral formulation of HECPT in soft gelatin capsules (comprised of gelatin/glycerin/sorbitol/purifiers/purified water) containing 1.0 pan of HECPT in a vehicle comprising citric acid 0.1 to 0.9 parts by weight, purified water 1 pan by weight, glycerin 1 to 10 parts by weight, polyethylene glycol (molecular weight 200 to 300) 5 to 9 parts by weight, dehydrated ethyl alcohol 10 to 20% by weight of total solution weight, sodium acetate 0.05 to 0.5 parts by weight, a surfactant, and 1 to 10 parts dimethylisosorbide. A more preferred oral formulation will include as a surfactant pluronic F-127 poloxamer using 0.05 to 1.0 parts by weight.

Another preferred oral formulation will include the addition of taurocholic acid 2 to 10 parts by weight. The soft gelatin capsules may also be composed of any of a number of compounds used for this purpose including, for example, a mixture of gelatin, glycerin, sorbitol, purified water, and parabens.

The table below indicates parts by weight of different components to be included in the oral formulation to be administered in capsules. Four components are marked with an "**" which denotes that the components are "optional." For the purpose of this invention, inclusion of these components depends on a variety of different factors; i.e. type of cancer the patient has, pretreated previously, etc.

| Ingredients | Parts by Weight |
| --- | --- |
| 10-hydroxy 7-ethyl Camptothecin | 1 |
| Citric Acid | 0.1–0.5 |
| Purified Water | 0.5–1.5 |
| Glycerin** | 0.4–2 |
| PEG 300 | 5–9 |
| EtOH** | 10–20% by weight of total solution weight |
| Dimethylisosorbide | 1–10 |
| Poloxamer surfactant (Pluronic F-127)** | 0.05–1.0 |
| Sodium Acetate | 0.05–0.5 |
| Taurocholic Acid** | 2–10 |

Clinicians will administer HECPT to human patients with cancer according to schedules that maximize its potential antitumor effects and diminish its potential toxic side effects. Except at extremely high doses which produce high plasma concentrations of the drugs, the antitumor activity of CPT-11 and HECPT can be increased by increasing the duration of exposure (time dependent) rather than increasing the dose (dose dependent) of the drug. The greater antitumor effects associated with increasing the duration of exposure is a finding that is most likely related to the predominant S-phase mode of antitumor activity of CPT-11 and HECPT. HECPT is an S-phase-active agent; therefore, the greatest antitumor effect in humans will likely be observed with prolonged infusion or closely spaced repetitive administration schedules. Such schedules of administration would expose more cycling tumor cells to the drug and increase the frequency of exposure of the tumor cells in S-phase to sufficiently toxic levels of the drug.

A further embodiment of this invention is that the claimed HECPT composition or claimed HECPT dissolved in DMI or dissolved in DMA can be used in a variety of different cancer types. The claimed formulations and compositions of the invention may be used in treatment of a number of tumors including, without limitation, human cancers of the lung, breast, colon, prostate, melanoma, pancreas, stomach, liver, brain, kidney, uterus, cervix, ovaries, and urinary tract.

The site and type of tumor to be treated will, in many cases, influence the preferred route of administration and therapeutic regimen to be applied. Consequently, although the formulations of the invention may be most usually administered by intravenous injection or infusion, they also can be delivered directly into the tumor site or by other methods designed to target the drug directly to the tumor site. For example, in patients with malignant pleural effusion, the intrapleural route may be preferred; in patients with poor venous access the subcutaneous route of administration may be preferred; in patients with primary or metastatic cancer involving the brain or nervous system, the intracisternal or intrathecal route of administration may be most advantageous; in patients with malignant ascites secondary to cancer, one may select intraperitoneal administration; and in patients with bladder cancer direct intravesicular instillation may be most advantageous. Similarly, in tumors of the skin, the formulation may be topically applied. An oral formulation is also provided for use where suitable.

Thus, an additional embodiment of this invention is an HECPT solution comprising HECPT dissolved in DMI or DMA, in the presence of a pharmaceutically acceptable acid and this solution is sterilized and prepared for oral, intrapleural, intrathecal, subcutaneous, intracisternal, intravesicular, intraperitoneal, topical or parenteral administration to a patient with cancer.

The formulations of the claimed invention may also be used in conjunction with other drugs in methods of convergent therapy whereupon an additional drug or drugs are co-administered along with the claimed HECPT composition. Thus, HECPT may be co-administered with CPT-11, topotecan, camptothecin, or 10,11 methylenedioxy camptothecin, using a pharmaceutically acceptable carrier, and the co-administration is based on an optimal dosage and schedule. For example, in a preferred embodiment, CPT-11 may be co-administered with HECPT. Also, HECPT may be co-administered with a combination of CPT-11, topotecan, camptothecin, and 10, 11 methylenedioxy camptothecin, using a pharmaceutically acceptable carrier, and the co-administration is based on an optimal dosage and schedule. For example, CPT-11 and topotecan may be co-administered with the claimed HECPT.

A further embodiment of claimed HECPT is a method of treatment of cancer in humans with convergent therapy or combination therapy. This method uses 10-hydroxy 7-ethyl camptothecin dissolved in dimethylisosorbide (DMI) or dimethylacetamide in (DMA), in the presence of pharmaceutically acceptable acid and co-administers it with additional drugs selected from the group consisting of, but not limited to, carmustine, azathioprine, cisplatinum, carboplatin, iproplatin, cyclophosphamide, ifosfamide, etoposide, ara-C, doxorubicin, daunorubicin, nitrogen mustard, 5-fluorouracil, bleomycin, mitomycin-C, fluoxymesterone, mechlorethamine, teniposide, hexamethylmelamine, leucovorin, melphelan, methotrexate, mercaptopurine, mitoxantrone, BCNU, CCNU, procarbazine, vincristine, vinblastine, vindesine, thioTEPA, amsacrine, G-CSF, GM-CSF, erythropoietin, γ-methylene-10-deazaaminopterin or ,γ-methylene-10-ethyl-10-deazaaminopterin, taxol, and 5-azacytidine. For the purpose of this invention, the terms convergent, co-administered, and combination are used interchangeably.

HECPT in DMI or DMA when administered parenterally, is preferably diluted with an appropriate volume of a parenteral vehicle to a concentration of about 0.1 mg/ml or lower of HECPT activity. A further embodiment of the claimed invention is a sterile solution of any of the claimed HECPT compositions and formulations for sterile administration to a patient with cancer upon dilution with a sterile parenteral vehicle. For the purposes of this invention, parenteral vehicles include dextrose 5 to 10% in water, 0.9% NaCl in water with or without 5% or 10% Dextrose, 0.45%NaCl in water with or without 5% or 10% Dextrose, and 3%NaCl in water with or without 5% to 10% Dextrose, or sterile lipid formulations, such as intralipid, used for parenteral nutritional support for cancer patients.

DETAILED DESCRIPTION OF PREFERRED EMBODIMENTS

In its preferred embodiments, this invention involves preparation and administration of novel lactone stable HECPT formulations as described below.

EXAMPLES

The following examples illustrate selected modes for carrying out the claimed invention and are not to be construed as limiting the specification and claims in any way.

Example 1

For injection or infusion into aqueous body fluids, a formulation comprises from about 0.1 to about 2.0 mg of HECPT dissolved in 1 to 10 parts of dimethylisosorbide in an acidified vehicle comprising between about 10 to about 40 percent of an acceptable alcohol, about 4 to about 10 parts by weight of polyether glycol, and about 1 to about 10 parts of a non-ionic surfactant. Suitable alcohols include dehydrated ethyl alcohol, benzyl alcohol. Suitable polyether glycols, include polyethylene glycol 200, polyethylene glycol 300, propylene glycol. Suitable non-ionic surfactants include polysorbate-80. In a preferred embodiment, the formulation of HECPT is supplied as an intravenous injectable in a 1 mg vial comprising a sterile, nonaqueous solution of drug in a vehicle comprising dehydrated ethyl alcohol, benzyl alcohol, citric acid, polyethylene glycol 300, and polysorbate (Tween 80) in acidified medium with a pH of 3 to 4 at a final concentration of 1 mg per 1 to 2 ml.

Example 2

A second formulation comprises from about 0.1 mg to about 2.0 mg of HECPT in an acidified vehicle comprising between about 0.1 to 2 parts of an alcohol and about 1 to 10 parts of a non-ionic surfactant. Suitable alcohols include dehydrated ethyl alcohol USP, and benzyl alcohol. Suitable non-ionic surfactants include the polyoxyethylated oils, such as polyoxyethylated vegetable oils, such as castor oil, peanut oil, and olive oil. In a preferred embodiment 0.1 mg to 2 mg HECPT is formulated in 1 to 10 parts of dimethylisosorbide, 1 to 10 parts of Cremaphor EL (polyoxyethylated castor oil), 0.1 to 2 parts by weight dehydrated ethyl alcohol USP, and 0.1 to 0.9 parts citric acid to adjust the final pH between 3 to 4.

Example 3

An oral formulation of HECPT in soft gelatin capsules (comprised of gelatin/glycerin/sorbitol/purifiers/purified water) containing 1.0 part of HECPT in 1 to 10 parts of dimethylisosorbide, citric acid 0.1 to 0.5 parts by weight, purified water 1 part by weight, glycerin 1 to 10 parts by weight, and polyethylene glycol 200 to 300 5 to 9 parts by weight, dehydrated ethyl alcohol 0.2 to 2 parts by weight of total solution weight, sodium acetate 0.05 to 0.5 parts by weight, pluronic F-127 poloxamer using 0.05 to 1.0 parts by weight, and taurocholic acid 2 to 10 parts by weight. The soft gelatin capsules may also be composed of any of a number of compounds used for this purpose including, for example, a mixture of gelatin, glycerin, sorbitol, purified water, and parabens.

To prolong the stability and solubility of HECPT for clinical infusions, the drug may diluted in 5 % Dextrose in water (D5W) to a final concentration of 0.001 mg/ml to about 0.1 mg/ml of HECPT prior to injection or infusion.

Maintaining an acidic pH (3 to 4) in the formulation is particularly important to reduce the slow conversion of HECPT lactone to the E-ring-hydrolyzed carboxylate, which occurs at physiological pH. At equilibrium under physiologic pH, the ratio of the open-ring form to lactone increases. Hydrolysis of the lactone ring will be substantially reduced if the drug is kept in an acidic environment. Some of the unpredictable toxicity seen in earlier clinical trials using sodium camptothecin may have been due to the formation of greater amounts of the lactone form of camptothecin, which is 10-fold more toxic than sodium camptothecin in mice. The lactone form of camptothecin, as in HECPT, is less water soluble than the carboxylate E-ring form. When early clinical trials were first conducted with camptothecin using NaOH, the significance of maintaining the closed lactone ring for uniform efficacy in treating patients with cancer was poorly understood. The early reported unpredictable clinical toxicities associated with camptothecin administration may have been exacerbated by the NaOH formulation which promotes the formation of the carboxylate form, and by the relative lack of understanding of the significance of the lactone form of camptothecin as it relates to antitumor activity.

The foregoing description of the formulation invention has been directed to particular preferred embodiments in accordance with the requirements of the patent statutes and for purposes of explanation and illustration. Those skilled in the art will recognize that many modifications and changes may be made without departing from the scope and the spirit of the invention.

Initially, patients may be treated in a dose escalation protocol to determine the maximal tolerated dose of the HECPT formulation. In determining a safe starting dose for HECPT, the data from Tables 3 and 4 are helpful. For the purpose of this invention, "AUC" is defined as "area under the curve" and "CpMax" is defined as "the maximum plasma concentrate at the end of I.V. infusion."

TABLE 3

| | Analysis of AUC and CpMax Ratios of CPT-11:HECPT | | | | |
|---|---|---|---|---|---|
| | AUC CPT-11 (ug × hr/ml) | AUC HECPT (ug × hr/ml) | Ratio AUC CPT-11/HECPT | CpMax CPT-11:HECPT (ug/ml) | CpMax Ratio CPT 11:HECPT |
| Ohe et al. | | | | | |
| 25 mg/m²/d × 5 | 14.1 | 1.08 | 13.0 | 1.178:0.0104 | 11.3:1 |
| 30 mg/m²/d × 5 | 20.5 | 0.96 | 21.3 | 1.500:0.0105 | 14.2:1 |

TABLE 3-continued

Analysis of AUC and CpMax Ratios of CPT-11:HECPT

| | AUC CPT-11 (ug × hr/ml) | AUC HECPT (ug × hr/ml) | Ratio AUC CPT-11/HECPT | CpMax CPT-11:HECPT (ug/ml) | CpMax Ratio CPT 11:HECPT |
|---|---|---|---|---|---|
| 35 mg/m²/d × 5 | 20.5 | 0.91 | 22.5 | 1.538:0.0068 | 22.6:1 |
| 40 mg/m²/d × 5 Rothenberg et al. | 28.5 | 0.86 | 33.1 | 2.043:0.0080 | 25.5:1 |
| 50 mg/m²/wk × 4 | 1.13 | 0.0622 | 18.1 | 0.89:0.0264 | 33.7:1 |
| 100 mg/m²/wk × 4 | 2.23 | 0.2148 | 10.4 | 1.29:0.0316 | 98.0:1 |
| 125 mg/m²/wk × 4 | 2.97 | 0.1955 | 15.2 | 1.70:0.0393 | 43.2:1 |
| 150 mg/m²/wk × 4 | 2.81 | 0.1232 | 22.8 | 1.56:0.0367 | 42.5:1 |
| 180 mg/m²/wk × 4 | 3.83 | 0.2328 | 16.5 | 1.97:0.0262 | 75.2:1 |

TABLE 4

Fractional Amounts of Lactone Species of CPT-11 and HECPT as Function of Increasing Single Dose I.V. From Rothenberg et. al.

| Dose | CPT-11 AUC Based | HECPT AUC Based | CPT-11 CpMax Based | HECPT CpMax Based |
|---|---|---|---|---|
| 50 mg/m² | 0.41 | 0.29 | 0.51 | 0.50 |
| 80 mg/m² | 0.30 | 0.50 | 0.44 | 0.39 |
| 100 mg/m² | 0.33 | 0.58 | 0.53 | 0.45 |
| 125 mg/m² | 0.39 | 0.43 | 0.55 | 0.41 |
| 150 mg/m² | 0.33 | 0.30 | 0.42 | 0.36 |
| 180 mg/m² | 0.33 | 0.63 | 0.42 | 0.45 |

Data obtained using the continuous infusion schedule of Ohe et al. shows that the ratio CPT-11 to HECPT AUCs increases gradually as a function of dose and that this increase is substantially more marked in a single dose study. The data in Table 3 supports the conclusion that conversion of CPT-11 to HECPT is a saturable process which is variable among patients, and that increases in the dose (e.g., above 30 mg/m²/d) of CPT-11 can result in a decrease in the CpMax of HECPT using a 5 day continuous infusion schedule. Although the factors involved in interpatient variability is not completely understood, some variability in the pharmacology and metabolic conversion of CPT-11 to HECPT probably exists based on the pharmacologic data reported from several investigators. This variability in the conversion of CPT-11 to HECPT is likely to be a result in instances of unexpected toxicity or lack of clinical effect by the use of CPT-11. In Table 4, the overall fractional concentration of the lactone species of CPT-11 and HECPT appear to remain fairly constant through a range of doses.

The administration of HECPT may be carried out using various schedules and dosages. For example:

1. For intravenous administration, a suitable dose is 0.45 mg to 5.4 mg/m² per day using a 3 to 5 day continuous infusion schedule every 21 to 30 days or 2.7 to 32.4 mg/m² given as a 30 to 90 minute infusion every 21 to 30 days.
2. Another schedule involves the administration of 1.2 to 15.5 mg/m² daily for three consecutive days over 90 minutes intravenously every 21 to 28 days.
3. A suitable oral dose of the drug is 0.5 to 50 mg/m² per day using the lower dose for a period of 3 to 5 days and using divided dosages of administration of two to four times per day.

The parenteral and oral doses can be administered under the supervision of a physician based on gradual escalation of the dosage to achieve the maximum tolerated dose in the individual patient. The oral administration schedule of HECPT may involve multiple daily doses or single daily doses for one or more consecutive days with the ability of the physician to optimize therapy by reaching the maximum effective antitumor dose that has the least toxicity in the individual patient.

In addition, patients may be given the lactone stable HECPT as an inpatient or outpatient using the following exemplary schedules:

1) 2.7 to 32.4 mg/m² given over 90 minutes I.V. every 21 to 28 days;
2) 1.2 to 15.5 mg/m² given daily for three consecutive days over 90 minutes I.V. every 21 to 28 days;
3) 1.0 to 20.0 mg/m² week given once per week X 3 consecutive weeks over 90 minutes I.V. with 2 weeks rest after each 3 week cycle for pretreated patients;
4) 2.25 to 24.3 mg/m² given once per week X 3 consecutive weeks over 90 minutes I.V. for previously untreated patients with 2 weeks rest after each 3 week cycle; and
5) 0.45 to 5.4 mg/m²/d X 3 to 5 consecutive days as a continuous I.V. infusion every 21 to 28 days.

In a preferred embodiment, HECPT is initially given at a lower dose. The dose of HECPT is then escalated at each successive cycle of treatment until the patient develops side effects which demonstrates individual therapeutic tolerance. The purpose of dose escalation is to safely increases the drug levels to a maximum tolerated dose and should result in increased cytotoxicity and improved antitumor activity.

Dosages can be escalated based on patient tolerance as long as unacceptable toxicity is not observed. "Unacceptable toxicity" is defined by World Health Organization (WHO) as grade 3 non-hematologic toxicity excluding nausea and vomiting and grade 4 vomiting or hematologic toxicity according to the National Cancer Institute common toxicity criteria. Since some clinical drug toxicity is anticipated in routine clinical oncology practice, appropriate treatment will be used to prevent toxicity (e.g., nausea and vomiting) or ameliorate signs and symptom if they are observed (e.g., diarrhea). For example, antiemetics will be administered for nausea and vomiting, antidiarrheals for diarrhea, and antipyretics for fever. Appropriate dosages of steroids/ antihistamines will also be used to prevent or ameliorate any anaphylactoid toxicity if an anaphylactoid reaction is observed.

Kaneda's HPLC method and further modifications by Barilero et al. are useful for the measuring quantities of HECPT in plasma and tissue. In these assays, plasma, serum, and tissue homogenate samples containing HECPT are immediately diluted 10-fold with 0.1N HCL to give final concentrations of about 100ng/ml for HECPT. The diluted plasma or serum samples are applied to a C18 cassette of an automated sample processor (Analytichem International, Harbor City, Calif.), which is activated with 1.5 ml of methanol and water. The HPLC apparatus (Model LC-4A; Shimadzu Seisakusho) is linked to the automated sample processor, and a C18 reversed-phase column (LiChrosorb RP-18; 25×0.4 cm; Merck) with an RP-18 precolumn is used for chromatography. The mobile phases consists of $CH_3CN$/water (¼, v/v) for HECPT. The flow rate and column temperature are 2.0 ml/min and 60 degrees Celsius for HECPT. A fluoro-spectromonitor (Model RF-530; Shimadzu Seisakusho) is set at an excitation wavelength of 373 nm and an emission wavelength of 380 nm and a wavelength of 540 nm for HECPT. The peak area is integrated by a data processor (Model C-RIBS Chromatopac; Shimadzu Seisakusho). HECPT gives retention times of 13.8 min. Calibration curves are established for each determination by 10% mouse serum in 0.1N HCL containing HECPT. Validations of HECPT determinations will be made by running samples versus real standards. The limit of determination is about 1 to 5 ng for HECPT using this assay.

REFERENCES

The following references may facilitate understanding or practice of certain aspects of the present invention. Inclusion of a reference in this list is not intended to and does not constitute an admission that the reference represents prior art with respect to the present invention.

| U.S. Pat. No. | | |
|---|---|---|
| 4,545,880 | 10/85 | Miyasaka et al. |
| 4,473,692 | 9/84 | Miyasaka et al. |
| 4,778,891 | 10/88 | Tagawa et al. |
| 5,061,800 | 10/91 | Miyasaka et al. |

Other Publications

Barilero et al., *Simultaneous Determination of the Camptothecin Analogue CPT-11 and Its Active Metabolite HECPT by High Performance Liquid Chromatography: Application to Plasma Pharmacokinetic Studies in Cancer Patients.* J. Chromat. 575:275–280; 1992.

Bates et al., *Solubilizing Properties of Bile Salt Solutions. I. Effect of Temperature and Bile Salt Concentration On Solubilization of Glutethimide, Griseofulvin and Hexestrol.* Journal of Pharmaceutical Sciences, 55:191–199, (1966).

Bates et al., *Rates of Dissolution of Griseofulvin and Hexestrol in Bile Salt Solutions.* Chem. Abstracts 65:8680b, 1966.

Bates et al., *Solubilizing Properties of Bile Salt Solutions on Glutethimide, Griseofulvin, and Hexestrol.* Chem. Abstracts 64:9517e 1966; 65:15165a, 1966.

Clavel, M. et al., *Phase I Study of the Camptothecin Analogue CPT-11, Administered Daily for 3 Consecutive Days.* Proc. Amer. Assoc. Cancer Res. 3:83, 1992.

Culine, S., *Phase I Study of the Camptothecin Analog CPT-11, Using a Weekly Schedule.* Proc. of Amer. Soc. Clin. Onc. 11:110, 1992.

Fukuoka, M. et al., *A Phase II Study of CPT-11, A New Derivative of Camptothecin, for Previously Untreated Small-Cell Lung Cancer.* J. Clin. One. 10(1):16–20, 1992.

Giovanella B. C., et al., *DNA Topoisomerase I—Targeted Chemotherapy of Human Colon Cancer in Xenografts.* Science 246:1046–1048; 1989.

Hsiang et al., *Arrest of Replication Forks by Drug-stabilized Topoisomerase I-DNA Cleavable Complexes as a Mechanism of Cell Killing by Camptothecin Analogues.* Cancer Res. 49:5077–5082, 1989.

Jaxel, C. et al., *Structure Activity Study of the Actions of Camptothecin Derivatives on Mammalian Topoisomerase I: Evidence for a Specific Receptor Site and a relation to Antitumor Activity.* Cancer Res. 49:1465–1469, 1989.

Kaneda, N. et al., *Metabolism and Pharmacokinetics of the Camptothecin Analogue CPT-11 in the Mouse.* Cancer Research 50:1715–1720, 1990.

Kano Y., et al., *Effects of CPT-11 in Combination with other Anti-Cancer Agents in Culture.* Int. I. Cancer 50:604–610;1992.

Kanzawa F., et al., *Role of Carboxylesterase on Metabolism of Camptothecin Analog (CPT-11) in Non-Small Cell Lung Cancer Cell Line PC-7 Cells (Meeting Abstract).* Proc. Annual Meet. Pan. Assoc. Cancer Res. 33:A2552; 1992.

Kawato, Y. et at., *Intracellular Roles of HECPT, a Metabolite of the Camptothecin Derivative CPT-11, in the Antitumor Effect of CPT-11.* Cancer Res. 51:4187–4191, 1991.

Kunimoto, T. et at., *Antitumor Activity of 7-Ethyl-10-[4-(1-piperidino)-1-piperidino] Carbonyloxy-Camptothecin, a Novel Water Soluble Derivative of Camptothecin Against Murine Tumors.* Cancer Res. 47:5944–5947, 1987.

Malone et at., *Desoxycholic Acid Enhancement of Orally Administered Reserpine.* Journal of Pharmaceutical Sciences, 55:972–974 (1966).

Masuda, N. et at., *CPT-11: A New Derivative of Camptothecin for the Treatment of Refractory or Relapsed Small-Cell Lung Cancer.* J. Clin. Onc. 10(8):1225–1229 1992.

Negoro, S. et al., *Phase I Study of Weekly Intravenous Infusions of CPT-11, a New Derivative of Camptothecin, in the Treatment of Advanced Non-Small Cell Lung Cancer.* JNCI 83(16):1164–1168, 1991.

Negoro, S. et al., *Phase II Study of CPT-11, New Camptothecin Derivative, in Small Cell Lung Cancer.* Proc. of Amer. Soc. Clin. Onc. 10:241, 1991.

Niimi S., et al., *Mechanism of Cross-Resistance to a Camptothecin Analogue (CPT-11) in a Human Ovarian Cancer Cell Line Selected by Cisplatin.* Cancer Res. 52:328–333; 1992.

Ohe, Y. et al., *Phase I Study and Pharmacokinetics of CPT-11 with 5-Day Continuous Infusion.* JNCI 84(12):972–974, 1992.

Ohno, R. et al., *An Early Phase H Study of CPT-11: A New Derivative of Camptothecin, for the Treatment of Leukemia and Lymphoma.* J. Clin. Onc. 8(11):1907–1912, 1990.

Pommier, Y. et al., *Camptothecins: Mechanism of Action and Resistance (Meeting Abstract).* Cancer Investigation, Presented at the "Chemotherapy Foundation Symposium X Innovative Cancer Chemotherapy for Tomorrow," page 3, 1992.

Rothenberg, M. L. et al., *A Phase I and Pharmacokinetic Trial of CPT-11 in Patients with Refractory Solid Tumors.* Amer. Soc. Clin. Onc. 11:113, 1992.

Rothenberg, M. L., Kuhn, J. G., Burris, H. A., Nelson, J., Eckardt, J. R., Tristan-Morales, M., Hilsenbeck, S. G., Weiss, G. R., Smith, L. S., Rodriguez, G. I., Rock, M. K., Von Hoff, D. D. *Phase I and Pharmacokinetic Trial of Weekly CPT-11.* Journal of Clinical Oncology. 11:2194–2204 (1993).

Rowinsky, E. et al., *Phase I Pharmacologic Study of CPT-11, A Semisynthetic Topoisomerase I-Targeting Agent, on a Single-Dose Schedule* (Meeting Abstract). Proc. of Amer. Soc. Clin. Onc. 11:115, 1992.

Sawada S. et al., *Synthesis and Antitumor Activity of 20 (S) -Camptothecin Derivatives: Carbonate-Linked, Water Soluble, Derivatives of 7-Ethyl-10-hydroxycamptothecin.* Chem. Pharm. Bull. 39:14446–1454; 1991.

Shimada, Y. et al., *Phase II Study of CPT-11, New Camptothecin Derivative, In the Patients with Metastatic Colorectal Cancer.* Proc. of Amer. Soc. Clin. Onc. 10:135 35, 1991.

Takeuchi, S. et al., *Late Phase II Study of CPT-11, A Topoisomerase I Inhibitor, In Advanced Cervical Carcinoma (CC)* (Meeting Abstract). Proc. of Amer. Soc. Clin. Onc. 11:224, 1992.

Westergaard et al., *The Mechanism Whereby Bile Acid Mycelles Increase the Rate of Fatty Acid and Cholesterol Uptake Into the Intestinal Mucosal Cell.* Journal of Clinical Investigation, 58:97–108 (1976)).

The foregoing description has been directed to particular embodiments of the invention in accordance with requirements of the Patent Statutes for the purposes of illustration and explanation. It will be apparent, however, to those skilled in this art, that many modifications, changes and variations in the claimed antitumor compositions, solutions, methods of administration of the antitumor compositions set forth will be possible without departing from the scope and spirit of the claimed invention. It is intended that the following claims be interpreted to embrace all such modifications and changes.

What is claimed is:

1. A 10-hydroxy 7-ethyl camptothecin solution consisting essentially of an effective amount of 10-hydroxy 7-ethyl camptothecin dissolved in dimethylisosorbide and a pharmaceutically acceptable acid wherein said acid is an organic carboxylic acid selected from the group consisting of citric acid, and taurocholic acid in an admixture with citric acid.

2. The solution of claim 1 wherein said solution is sterilized and prepared for oral, intrapleural, intrathecal, intracisternal, intravesicular, intraperitoneal, topical or parenteral administration to a patient with cancer.

3. The solution of claim 1 wherein said organic carboxylic acid is citric acid.

4. The solution of claim 1 wherein said solution has from 0.1 mg to 5.0 mg activity of 10-hydroxy 7-ethyl camptothecin per ml of solution.

5. An antitumor composition consisting essentially of a solution of 10-hydroxy 7-ethyl camptothecin dissolved in dimethylisosorbide having from 0.1 mg to 100 mg 10-hydroxy 7-ethyl camptothecin activity per ml and from 0.1 to 0.9 part by weight of a pharmaceutically acceptable organic carboxylic acid per part by weight of 10-hydroxy 7-ethyl camptothecin wherein said organic carboxylic acid is selected from the group consisting of citric acid, and taurocholic acid in an admixture with citric acid.

6. The antitumor composition of claim 5 wherein said organic carboxylic acid is citric acid.

7. The antitumor composition of claim 5 wherein said part by weight of a pharmaceutically acceptable organic carboxylic acid is from 0.05 to 0.1 part by weight per part by weight of 10-hydroxy 7-ethyl camptothecin.

8. An antitumor composition consisting essentially of a solution of 10-hydroxy 7-ethyl camptothecin dissolved in dimethylisosorbide, a pharmaceutically acceptable acid selected from the group consisting of citric acid and taurocholic acid in an admixture with citric acid or a pharmaceutically acceptable salt thereof, polyethylene glycol, water, glycerin and a lower alcohol selected from the group consisting of ethyl alcohol and ethyl alcohol in an admixture with benzyl alcohol.

9. The antitumor composition of claims 8 and 14 wherein said polyethylene glycol has a molecular weight of 300.

10. The solution of claims 1, 8, or 14 wherein said solution is encapsulated within a hard gelatin capsule.

11. The solution of claims 1, 8, or 14 wherein said solution is encapsulated within a soft gelatin capsule.

12. The antitumor composition of claim 8 wherein said solution has for each part by weight of 10-hydroxy 7-ethyl camptothecin, 1–10 parts by weight of dimethylisosorbide, 0.005–0.5 parts by weight of a pharmaceutically acceptable acid selected from the group consisting of citric acid, and 1–10 parts by weight of taurocholic acid in an admixture with citric acid or a pharmaceutically acceptable salt thereof, 1–10 parts by weight of polyethylene glycol, and 0.1–2.0 parts by weight water.

13. The antitumor composition of claim 8 wherein said acid is citric acid.

14. An antitumor composition consisting essentially of a solution of 10-hydroxy 7-ethyl camptothecin dissolved in dimethylisosorbide, a pharmaceutically acceptable acid selected from the group consisting of citric acid, and taurocholic acid in an admixture with citric acid or a pharmaceutically acceptable salt thereof, polyethylene glycol, water, ethanol, glycerin, and a buffer.

15. The antitumor composition of claim 14 wherein said solution has for each part by weight of 10-hydroxy 7-ethyl camptothecin, 1–10 parts by weight of dimethylisosorbide, 0.005–0.5 parts by weight of a pharmaceutically acceptable acid selected from the group consisting of citric acid, and 1–10 parts by weight of taurocholic acid in an admixture with citric acid or a pharmaceutically acceptable salt thereof, 1–10 parts by weight of polyethylene glycol, 0.1–2 parts by weight of glycerin, 0.1–2 parts by weight of ethanol, 0.005–0.5 parts of a buffer, and 0.1–2.0 parts by weight water.

16. An antitumor composition consisting essentially of a solution of 10-hydroxy 7-ethyl camptothecin dissolved in dimethylisosorbide, a pharmaceutically acceptable acid selected from the group consisting of citric acid, and taurocholic acid in an admixture with citric acid, a lower alcohol, polyethylene glycol, and a surfactant.

17. The antitumor composition of claim 16 wherein said pharmaceutically acceptable organic acid is citric acid, wherein said polyethylene glycol has a molecular weight of 300, wherein said lower alcohol is ethanol and wherein said surfactant is polysorbate-80.

18. An antitumor composition consisting essentially of a solution of 0.1 mg to 2.0 mg of 10-hydroxy 7-ethyl camptothecin dissolved in 1 to 10 parts of dimethylisosorbide in the presence of 0.1 to 0.5 parts of a pharmaceutically acceptable organic carboxylic acid selected from the group consisting of citric acid, and taurocholic acid in an admixture with citric acid, wherein said solution further has 5 to 9 parts by weight of polyethylene glycol, 0.1 to 2.0 parts of a pharmaceutically acceptable alcohol, and 1 to 10 parts of a non-ionic surfactant.

19. The antitumor composition of claim 18 wherein said organic carboxylic acid is citric acid, wherein said polyethylene glycol has a molecular weight of 300, wherein said alcohol is ethanol and wherein said surfactant is polysorbate-80.

20. An antitumor composition consisting essentially of a solution 0.1 mg to 2.0 mg of 10-hydroxy 7-ethyl camptothecin dissolved in 1 to 10 parts of dimethylisosorbide in the presence of 0.1 to 0.5 parts of a pharmaceutically acceptable organic carboxylic acid selected from the group consisting of citric acid, and taurocholic acid in an admixture with citric acid, wherein said solution further has 0.1 to 2.0 parts of a pharmaceutically acceptable alcohol, and 1 to 10 parts of a non-ionic surfactant.

21. The antitumor composition of claim 20 wherein said acid is citric acid, wherein said alcohol is ethanol, and wherein said non-ionic surfactant is comprised of polyoxyethylated castor oil.

22. An antitumor composition consisting essentially of a solution of 0.1 mg to 2.0 mg of 10-hydroxy 7-ethyl camptothecin dissolved in 1 to 10 parts of dimethylisosorbide, wherein said solution further has 1 to 10 parts polyoxyethylated castor oil, 0.1 to 2 parts by weight dehydrated ethyl alcohol USP, and 0.1 to 0.9 parts citric acid.

23. A pharmaceutical formulation comprising an effective amount of 10-hydroxy-7-ethyl camptothecin, a quantity of dimethylisosorbide sufficient to form a solution or suspension, and an organic carboxylic acid in sufficient quantity to lower the pH of the solution to a value sufficient to stabilize the camptothecin in its active lactone form.

24. The pharmaceutical formulation of claim 23 wherein said acid is added in sufficient quantity to lower the pH to below 5.0.

25. The pharmaceutical formulation of claim 23 wherein the effective amount of said camptothecin is completely dissolved in the dimethylisosorbide.

26. The pharmaceutical formulation of claim 25 wherein the effective amount of said camptothecin is from 0.1 mg per mL of dimethylisosorbide to about 3.0 mg per mL of dimethylisosorbide.

27. The pharmaceutical formulation of claim 23, and further including one or more pharmaceutically acceptable diluents wherein the overall concentration of said camptothecin is about 0.1 mg per mL.

28. The pharmaceutical formulation of claim 27 wherein said pharmaceutically acceptable diluents are selected from the group consisting essentially of polyethylene glycol, ethyl alcohol, benzyl alcohol, polysorbate-80, polyoxyethylated castor oil, glycerin, poloxamer surfactant, sodium acetate, and water.

29. The pharmaceutical formulation of claim 23 wherein said organic carboxylic acid includes one or more acids selected from the group consisting of citric acid, gluconic acid, maleic acid, tartaric acid, succinic acid and fumaric acid.

30. The pharmaceutical formulation of claim 29 and further including a quantity of taurocholic acid or a pharmaceutically acceptable salt thereof.

* * * * *